United States Patent [19]

Levenson et al.

[11] 4,193,690

[45] Mar. 18, 1980

[54] HETERODYNE DETECTION OF COHERENT RAMAN SIGNALS

[75] Inventors: Marc D. Levenson; Gary L. Eesley, both of Los Angeles; William M. Tolles, Carmel; Jin-Joo Song, Whittier, all of Calif.

[73] Assignee: University of Southern California, Los Angeles, Calif.

[21] Appl. No.: 843,611

[22] Filed: Oct. 19, 1977

[51] Int. Cl.$^2$ .............................................. G01J 3/44
[52] U.S. Cl. .................................................. 356/301
[58] Field of Search .................................. 356/75, 301

[56] References Cited

PUBLICATIONS

"Raman-Induced Kerr Effect", Heiman et al., *Physical Review Letters*, vol. 36, No. 4, Jan. 26, 1976, pp. 189–192.
"Heterodyne Detection for Coherent Raman Spectroscopy", Eesley et al., *Bulletin of the American Physical Society*, Dec. 1, 1976, pp. 1287–1288.
"Coherent Raman Spectroscopy", Levenson, *Physics Today*, May 1977, pp. 44–47.
"Heterodyne Coherent Raman Spectroscopy", Eesley et al., *Digest of Technical Papers*, Jun. 1977, pp. 31 and 32.

*Primary Examiner*—F. L. Evans
*Attorney, Agent, or Firm*—Nilsson, Robbins, Dalgarn, Berliner, Carson & Wurst

[57] ABSTRACT

A method and apparatus for heterodyne detection of coherent Raman signals from a Raman active sample exhibiting a Raman-induced Kerr effect. More specifically, a method and apparatus is disclosed for generating a local oscillator output and heterodyning this output with a portion of a probe laser output having its polarization shifted by 90 degrees due to a Raman-induced Kerr effect in a Raman active sample. A probe laser output and a pump laser output are directed into and intersect within the Raman active sample. When their frequency difference is equal to a Raman mode frequency, a non-linear optically induced birefringence in the sample shifts the probe polarization and produces a signal at the output of a polarization analyzer. This signal is heterodyned with a local oscillator output having substantially the same frequency. The local oscillator output is generated either by rotating the polarization analyzer, elliptically polarizing the probe laser output or reflecting a portion of the probe laser output directly into an optical detector. A combining of the local oscillator output and the polarization-shifted probe laser output creates a heterodyned cross-term signal which is linearly proportional to the Raman cross-section of the sample. In addition, an apparatus is disclosed for modulation of the pump laser output which in turn modulates the heterodyned cross-term signal and facilitates its subsequent detection and amplification.

39 Claims, 4 Drawing Figures

HETERODYNE DETECTION OF COHERENT RAMAN SIGNALS

FIELD OF THE INVENTION

The invention relates to optical heterodyning methods and apparatus, and more particularly to optical heterodyning as it relates to the detection of coherent Raman signals.

BACKGROUND AND SUMMARY OF THE INVENTION

In 1928 Chandrasekhara Raman reported a process in which a material when irradiated with light would simultaneously absorb a photon at a first energy level and emit a photon at a second energy level. The energies of the two photons differed by an amount corresponding to the difference between two quantum-mechanical levels of the medium. Raman scattering, as the phenomenon came to be known, provided a tool for the spectroscopic investigation of energy levels not accessible by the usual absorption and emission techniques. For the first thirty-five years Raman scattering spectroscopy was very laborious, and was important more for the quantum-mechanical principles it illustrated than for its practical applications.

The development of coherent Raman spectroscopy, recently made possible by the availability of high powered tunable lasers, has provided a revolutionary new means for obtaining Raman spectra. Rather than randomly scattering photons as in earlier techniques, a medium can now be irradiated by a coherent light beam tuned over a predetermined frequency spectrum and the Raman modes studied through a beam of coherent radiation emitted from the medium which contains details of the Raman spectrum. Advantages of the coherent Raman techniques result because laser fields at two different frequencies can force a particular Raman mode of a medium to produce an oscillating dielectric constant which then interacts with one of the fields to produce a coherent output beam. The power in this beam can be many orders of magnitude larger than that in spontaneously scattered radiation and spatial filtering can be used to separate the output beam from unwanted radiation.

A recent development in Raman spectroscopy utilized a Kerr effect which is inducted in a scattering medium only at Raman-shifted frequencies. This Raman-induced Kerr effect is obtained when a strong polarized monochromatic pump beam at a frequency $w_1$ intersects within the medium a weak linearly polarized probe beam at a frequency $w_2$, thereby inducing complex, anisotropic changes in the refractive indices experienced by the weak probe beam. These changes exhibit resonances when $w_1-w_2$ is near a frequency of a Raman-active vibration in the scattering medium. Being anisotropic, the changes cause portions of the weak probe beam to shift polarization by 90 degrees as it passes through the scattering medium. A Glan-Thompson prism is oriented to pass only that portion of the probe beam whose polarization has thus shifted with respect to the original probe beam polarization. The output of the Glan-Thompson prism was typicallly analyzed with a spectrometer. Problems with Raman-induced Kerr effect spectroscopy (RIKES) arise because the intensity of the polarization-shifted probe beam is quadratic in the Raman cross-section of the medium and because there is a background linear in probe laser intensity which results from optical imperfections in sample cell windows, lenses, mirrors, etc., thereby obscuring the Raman modes.

This invention relates to methods and apparatus for greatly enhancing the sensitivity of existing coherent Raman spectroscopy techniques by heterodyning a Raman induced optical field with a stable local oscillator field. The result is a dramatic improvement in signal-to-noise ratio due to the creation of a heterodyned cross-term signal which is proportional to the product of the Raman-induced field and the local oscillator field and therefore linearly proportional to the Raman cross-section of the sample.

An apparatus for heterodyne detection of coherent Raman signals from a Raman active sample includes a pump laser having an output radiation at a frequency $w_1$ and a probe laser having an output radiation at a predetermined polarization and a frequency $w_2$, both laser outputs being directed into and intersecting within the sample. The pump laser frequency $w_1$ is set so that $w_1-w_2$ approximates a Raman mode frequency of the sample which, due to a Raman-induced Kerr effect in the sample, causes a portion of the probe laser output to shift polarization by 90 degrees. A polarization analyzer, such as a Glan-Thompson prism, is provided for passing portions of the probe laser output having a predetermined polarization after these portions have passed through the sample. Also included in the apparatus is a means for generating a local oscillator output having substantially the same frequency as that of the probe laser output and a means for heterodyning the local oscillator output with the probe laser output portion which shifted polarization. Means for detecting a heterodyned output portion proportional to the shifted probe laser output and the local oscillator output is also included.

In a first embodiment, the Glan-Thompson prism is oriented so that most of the probe laser output portion whose polarization has shifted by 90 degrees will be passed and some of the unshifted probe laser output will also be passed. The unshifted probe laser output constitutes in effect a local oscillator. The heterodyning of these two signals provides the heterodyned cross-term signal described above.

In a second embodiment a local oscillator output is generated by a retardation plate such as a quarter wave plate or a strained glass window, which is disposed to intersect the probe laser output prior to its entering the Raman-active sample. In this embodiment the Glan-Thompson prism is oriented so that only the polarization shifted portion of the probe beam will be passed. The retardation plate converts the linearly polarized probe laser beam to an elliptically polarized beam a portion of which has the same polarization as that of the probe laser output having the Raman-induced 90 degree polarity shift. This portion constitutes in effect a local oscillator output. Here the Glan-Thompson prism provides the heterodyning means by passing the above two outputs.

In a third embodiment a local oscillator output is obtained by reflecting a portion of the linearly polarized probe laser output prior to its entering the sample and routing it directly to the detector where it is heterodyned with the Glan-Thompson prism output. The reflected probe laser output is passed through a variable phase retarder plate so that its phase relative to the probe laser output can be adjusted.

In conjunction with the above local oscillator generating and heterodyning techniques, the invention also discloses modulation of the pump laser output so that the heterodyned cross-term signal will have predetermined modulation characteristics thereby enhancing isolation of the cross-term signal through signal processing techniques well developed in the art.

DETAILED DESCRIPTION

As required, detailed illustrative embodiments of the invention are disclosed herein. These embodiments exemplify the invention and are currently considered to be the best embodiments for such purposes. However, it is to be recognized that other optical heterodyning methods, probe and pump laser polarizations, and pump laser modulation techniques could be utilized. Accordingly, the specific apparatus and methods disclosed are representative only in providing a basis for the claims which define the scope of the invention.

Figure 1:
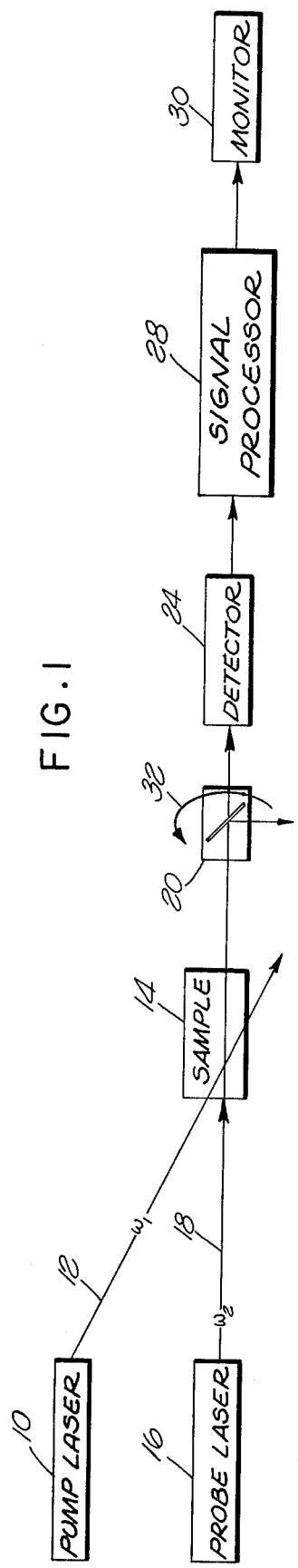
FIG. 1 is a block diagram of an apparatus according to a first embodiment of the invention for generating a heterodyned cross-term signal.

As above indicated, the invention discloses a method and apparatus for heterodyning a local oscillator output with portions of a probe laser output whose polarization has shifted 90 degrees due to a Raman-induced Kerr effect in a Raman-active sample thereby obtaining a heterodyned cross-term signal linearly proportional to the Raman cross-section of a Raman active sample. An apparatus for accomplishing the above is shown in FIG. 1. A pump laser 10 is provided having a circularly polarized output beam 12 at a frequency $w_1$ directed at a Raman-active sample 14 by a directing means such as an adjustable holding fixture (not shown). This output beam 12 could also be linearly or elliptically polarized. A probe laser 16 having a linearly polarized output beam 18 at a frequency $w_2$ is also directed at the Raman-active sample 14 so that the beam intersects a portion of the pump laser output 12 within the sample 14. The probe laser beam 18, having emerged from the sample 14, passes through a polarization analyzer 20 which in this embodiment is a Glan-Thompson prism. An optical detector 24 which could be a monochromatic type provides an output which is integrated and amplified by a signal processor 28. Its output is displayed on a monitor 30 which could be a oscillosope, strip chart recorder, etc.

In operation, the pump laser 10 is tuned so that the frequency difference between the pump laser output 12 and the probe laser output 18 ($w_1-w_2$) is equal to a Raman mode frequency of the sample 14. When this occurs, a nonlinear optically induced birefringence in the sample 14 causes a portion of the linearly polarized probe laser beam 18 to shift polarization by 90 degrees. In a typical Raman-induced Kerr effect spectroscopy (RIKES) experiment the polarization analyzer 20 is oriented so that only the portion of the probe laser beam 18 which changed polarization by 90 degrees is passed. However, according to this embodiment of the invention, the polarization analyzer 20 is rotated as shown in FIG. 1 at 32 so that some of the probe laser output 18 whose polarization was not shifted in the sample is also passed. This rotation is usually less than 15 degrees with respect to the orientation required to pass only the polarization shifted portion of the probe laser beam 18. The unshifted portion of the probe laser beam 18 which is passed by the polarization analyzer 20 constitutes in effect a local oscillator which mixes with the shifted portion, i.e. the Raman induced field, at the detector 24.

The intensity at the detector can be represented by the following equation:

$$I_D = |E_R + E_{LO}|^2 \\ = E_R^2 + 2E_R E_{LO} + E_{LO}^2$$

where
- $I_D$ = Intensity at the detector
- $E_R$ = Raman-induced field component
- $E_{LO}$ = Local oscillator field It will be appreciated that the $2E_R E_{LO}$ term, which can be referred to as a heterodyned cross-term signal, is linearly proportional to the Raman cross-section of the sample and the local oscillator field. If $E_{LO}$ is large with respect to $E_R$, considerable amplification of $E_R$ is obtained. For weak Raman modes the heterodyned cross-term signal will dominate over the Raman induced intensity $|E_R|^2$ which is quadratic in Raman cross-section. Additionally, the pump laser output beam 12 when modulated will in turn modulate the heterodyned cross-term signal as will be explained hereinbelow thereby making it easier to isolate with respect to residual background noise.

The output of the detector 24, one portion of which is the heterodyned cross-term signal, is routed to the signal processor 28 for smoothing and amplification. The smoothed and ampified heterodyned cross-term signal from the signal processor 28 drives one of many different types of possible monitoring devices 30.

The phase of the local oscillator created by rotation of the polarization analyzer 20 is the same as that of the probe laser beam 18 prior to its entrance into the sample 14. This coincidence of phase provides a heterodyned cross-term signal having amplitude characteristics as a function of frequency which are different from those obtained when the local oscillator phase differs by 90 degrees from that of the probe laser beam 18.

Figure 2:
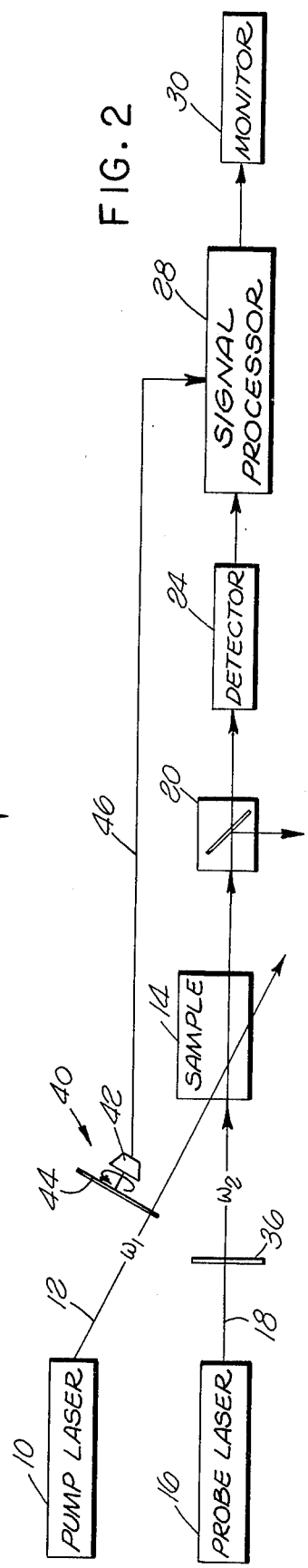
FIG. 2 is a block diagram of an apparatus according to a second embodiment of the invention for generating a heterodyned cross-term signal and a means for amplitude modulating the cross-term signal through amplitude modulation of the pump laser output.

An apparatus in accordance with a second embodiment for obtaining a 90 degrees phase shifted local oscillator is shown in FIG. 2. The pump laser 10, probe laser 16, sample 14, polarization analyzer 20, detector 24, signal processor 28 and monitor 30 are as previously described except that here the polarization analyzer 20 is oriented so that only a field having polarization orthogonal to the linearly polarized output 18 of the probe laser is passed.

A retardation plate 36, which could be a quarter wave plate or a strained glass window, is placed between the probe laser 16 and the Raman-active sample 14. The retardation plate 36 has the effect of converting polarization of the probe laser output beam 18 from the linear to elliptical. Again as $w_1-w_2$ approaches a Raman mode frequency, a portion of the elliptically polarized beam changes polarization by 90 degrees within the sample and can therefore be passed by the polarization analyzer 20. However, a portion of the elliptically polarized probe laser output 18 which has not changed polarization is also passed by the polarization analyzer, this passed portion constituting in effect the local oscillator. However, this local oscillator output, which is generated by the retardation plate 36, has a 90 degree phase shift with respect to the probe laser output 18 prior to its entrance into the sample 14. The remainder of the processing is the same as previously explained.

Also illustrated in this embodiment is an apparatus for amplitude modulating the heterodyned cross-term signal, the apparatus being equally applicable to the other embodiments described herein. It consists of a mechanical chopper 40 having a motor 42 and a rotating blade 44 which alternately blocks and unblocks the pump laser output 12. The modulation frequency is picked off from the motor 42 by any of a number of techniques well known in the art and routed via a connecting line 46 to the signal processor 28.

In operation, the rotating blade 44 induces an amplitude modulation on the pump laser output 12 which is cross-coupled into the polarization-shifted probe laser output. Specifically, when the pump laser output is present at the sample 14 there is a probe laser polarization shift; when it is not present there is no shift. This modulation is then induced through a heterodyning action on the heterodyned cross-term signal. The modulation is also transmitted on the connecting line 46 to the signal processor 28 which has been designed to isolate from its input those signals having the same modulation as an input reference modulation. Such amplifiers are well understood in the signal processing art.

In accordance with the above, many other modulation techniques could also be utilized. For example, one could use a pump laser operating in a pulsed mode, a pulsed laser in conjunction with a mechanical chopper or a mechanical chopper having differing light transmission characteristics as a function of angle of rotation. A frequency modulated laser could be utilized for the pump laser 10 thereby producing a heterodyned cross-term signal having a distinct frequency modulation characteristic. An electro-optical modulator commonly used in the art could be utilized in conjunction with the pump laser 10 to provide amplitude or polarization modulation to the pump laser output beam 12. A rotating quarter wave plate substituted for the rotating blade 44 would provide polarization modulation. Any one or a combination of these techniques could be utilized in conjunction with an appropriate signal processor 28 to enhance isolation of the heterodyned cross-term signal.

Figure 3:
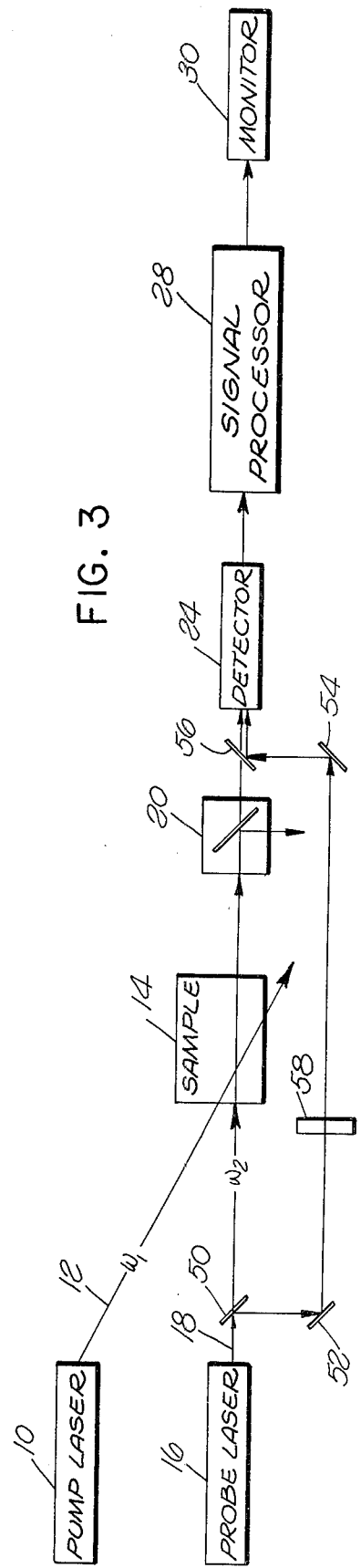
FIG. 3 is a block diagram of an apparatus according to a third embodiment of the invention for generating a heterodyned cross-term signal.
Figure 4:
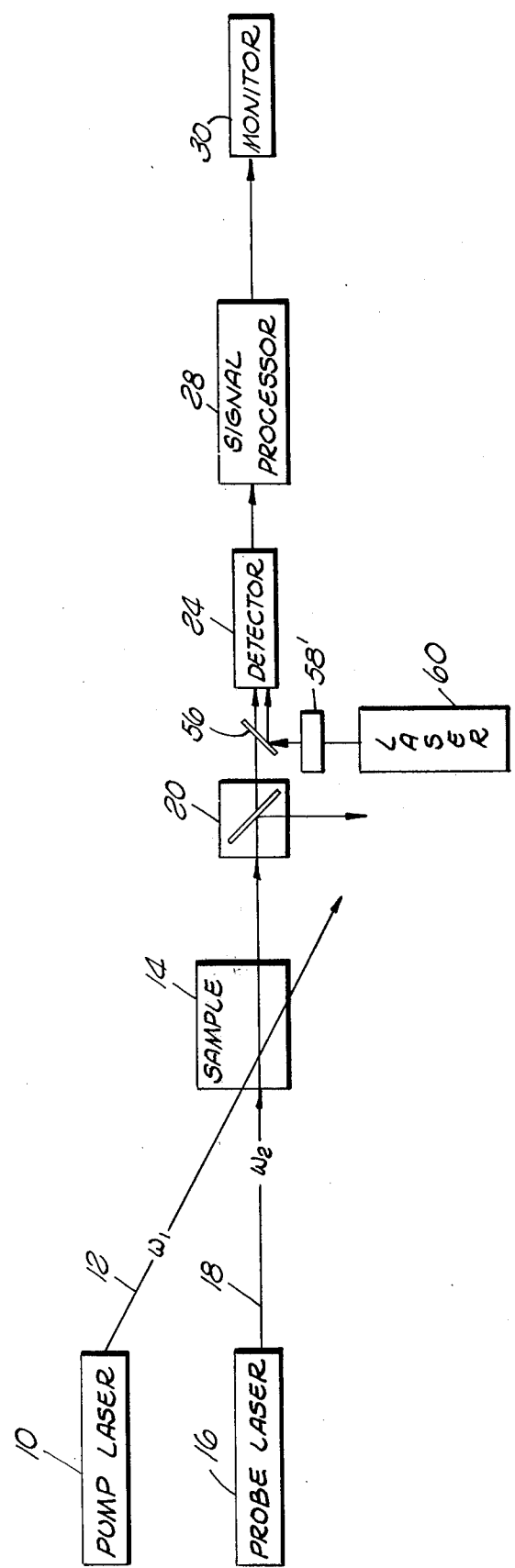
FIG. 4 is a block diagram of an apparatus according to still another embodiment.

A third embodiment for generating a local oscillator output is shown in FIG. 3. The elements are all as previously explained with the exception that a portion of the probe laser output beam is routed separately by reflection in turn from a first beam splitter 50, two reflecting plates 52 and 54 and a second beam splitter 56 towards the detector. It is desirable that the local oscillator output and the polarization analyzer 20 output enter the detector 24 colinearly. The combining of the thus routed local oscillator output with the polarization shifted portion of the probe laser output 18 passed by the polarization analyzer 20 at the detector 24 provides the heterodyned cross-term signal. It is important that the phase of the thus routed local oscillator output be known with respect to the phase of the probe laser. A variable phase retarder plate 58 is located in the local oscillator output between the reflecting plates 52 and 54 and is used to adjust the phase of the local oscillator output subsequent to the second beam splitter 56 so that it is either in phase or phase shifted by 90 degrees with respect to the phase of the probe laser output beam 18. Alternatively, as illustrated by FIG. 4, a third laser, shown in shadow as 60 and adjustable in phase by a phase retarder plate 58', could be directed at the detector 24 thereby providing a local oscillator and eliminting the need for the first beam splitter 50 and the reflecting plates 52 and 54. Preferably, the phase of the third laser output with respect to the phase of the probe laser output 18 should be coincident or offset by 90 degrees.

By way of exemplification, the foregoing methods and apparatus provide a capability to detect the Raman spectra of gases and the weak mode structure of biological molecules.

We claim:

1. In a method for detecting coherent Raman signals from a Raman active sample comprising the steps of irradiating said sample with a radiation output of a pump laser having a frequency $w_1$, irradiating said sample with a radiation output of a probe laser having a predetermined polarization and a frequency $w_2$, $w_1$-$w_2$ approximately a Raman mode frequency of said sample thereby resulting in a first portion of said probe laser output shifting polarization by 90 degrees as it passes through said sample, directing said probe laser output and said pump laser output into said sample whereby to intersect each other within said sample, filtering said probe laser output after passing through said Raman active sample whereby to pass only radiation having a predetermined polarization, and detecting said passed radiation, the improvement comprising the step of optically heterodyning said first portion of said probe laser output with a second laser output portion thereby obtaining a heterodyned cross-term signal linearly proportional to the Raman cross-section of said sample.

2. The improved method according to claim 1 in which said second laser output portion is obtained from a laser separate and apart from said probe laser, further comprising the step of adjusting the phase of said second laser output portion to have a predetermined relationship to the phase of said probe laser output.

3. The improved method according to claim 1 in which said second laser output portion is obtained from said probe laser.

4. The improved method according to claim 3 in which said probe laser output is linearly polarized.

5. The improved method according to claim 4 in which said filtering step is accomplished by a Glan-Thompson type prism oriented so that only radiation having said predetermined polarization is passed.

6. The improved method according to claim 5 further comprising the steps of:
    disposing said prism to allow passage of said shifted probe laser output and to provide blockage of said probe laser output not having the same polarization as said shifted probe laser output;
    routing a portion of said probe laser output prior to its entrance into said sample so as to bypass said sample and said prism;
    adjusting the phase of said probe laser routed portion to have a predetermined relationship to the phase of said probe laser output; and
    combining prior to said detecting step said routed portion with said shifted probe laser output after having passed through said prism, said routed portion of said probe laser output comprising a local oscillator output, said combining of said shifted probe laser output and said local oscillator output creating said heterodyned cross-term signal.

7. The improved method according to claim 6 in which said phase adjusting step comprises adjusting the phase of said probe laser routed portion so that said predetermined relationship is 90 degrees.

8. The improved method according to claim 4 in which said filtering step is accomplished by a Glan-Thompson type prism and further comprising the steps of:
   elliptically polarizing said probe laser output prior to its entrance into said sample;
   disposing said prism so as to pass said first portion of said probe laser output, also passing a portion of said probe laser output not having shifted polarization due to passage through said sample but having the same polarization as said shifted probe laser output, and to block all other portions of said probe laser output having passed through said Raman active sample; and
   combining said probe laser outputs having passed through said prism, said probe laser output portion not having shifted polarization comprising a local oscillator output, said combining forming said heterodyned cross-term signal.

9. The improved method according to claim 4 in which said filtering step is accomplished by a Glan-Thompson type prism and further comprising the steps of:
   disposing said prism so that a portion of said probe laser output and of said shifted probe laser output are passed, said passed portions having the same polarization, said passed probe laser output comprising a local oscillator output; and
   combining said passed portions thereby forming said heterodyned cross-term signal.

10. The improved method according to claim 1 in which said pump laser is circularly polarized.

11. The improved method according to claim 1 in which said pump laser is linearly polarized.

12. The improved method according to claim 1 further comprising the steps of:
   processing said heterodyned cross-term signal after said detecting step; and
   monitoring said processed heterodyned cross-term signal.

13. The improved method according to claim 12 further comprising the steps of:
   modulating said pump laser output thereby resulting in a modulated heterodyned cross-term signal; and
   selectively isolating said modulated heterodyned cross-term signal during said processing step.

14. The improved method according to claim 13 in which said modulating step comprises the step of amplitude modulating.

15. The improved method according to claim 13 in which said modulating step comprises the step of frequency modulating.

16. The improved method according to claim 13 in which said modulating step comprises the step of polarization modulating.

17. The improved method according to claim 1 in which said pump laser is a tunable laser.

18. In an apparatus for detecting coherent Raman signals from a Raman active sample comprising a pump laser having an output radiation at a frequency $w_1$, a probe laser having an output radiation at a predetermined polarization and a frequency $w_2$, $w_1-w_2$ approximating a Raman mode frequency of said sample thereby resulting in a first portion of said probe laser output shifting polarization as it passes through said sample, means for directing said probe laser output and said pump laser output into said sample whereby to intersect each other within said sample, a polarization analyzer for passing some of said probe laser radiation having a predetermined polarization after having passed through said sample, and means for detecting said probe laser radiation that has passed through said analyzer, the improvement comprising means for optically heterodyning said first portion of said probe laser output with a second laser output portion thereby obtaining a heterodyned cross-term signal linearly proportional to the Raman cross-section of said sample.

19. The improvement according to claim 18 in which said second laser output portion is obtained from a laser separate and apart from said probe laser, further comprising means to adjust the phase of said second laser output portion to have a predetermined relationship to the phase of said probe laser output.

20. The improvement according to claim 18 in which said second laser output portion is obtained from said probe laser.

21. The improvement according to claim 20 in which said probe laser output is linearly polarized and said first portion of said probe laser output is linearly polarized and shifted 90 degrees with respect to said probe laser output after having passed through said sample.

22. The improvement according to claim 21 in which said polarization analyzer is a Glan-Thompson type prism and said prism is disposed to allow passage of said shifted probe laser output and to provide blockage of that portion of said probe laser output which does not have the same polarization as said shifted probe laser output, and wherein said optical heterodyning means comprises means for routing a second portion of said probe laser output prior to its entrance into said sample directly to said detection means and bypassing said sample and said prism, said route portion comprising a local oscillator output, the combination of said shifted probe laser output and said routed portion at said detection means providing said heterodyned cross-term signal.

23. The improvement according to claim 22 further comprising means for shifting the phase of said probe laser second portion with respect to the phase of said probe laser output.

24. The improvement according to claim 23 in which said phase shifted means comprises a variable phase retarder plate through which said probe laser second portion passes, said phase retarder causing about a 90 degree phase shift with respect to the phase of said probe laser output.

25. The improvement according to claim 20 in which the polarization shift of said first portion is 90 degrees, and further comprising:
   means for elliptically polarizing said probe laser output before entrance into said sample, said polarization analyzer being a Glan-Thompson type prism, said prism being disposed to pass said first portion of said probe laser output, thereby also passing a portion of said probe laser output not having shifted polarization due to passage through said sample but having the same polarization as said shifted probe laser output, and to block all other portions of said probe laser output having passed through said sample; and said optical heterodyning means comprising said detection means whereby said passed probe laser output first portion and the portion of said passed probe laser output which does not have shifted polarization are combined thereat, said passed probe laser output not having shifted polarization constituting a local oscillator output, said passed probe laser outputs when combined forming said heterodyned cross-term signal.

26. The improvement according to claim 25 in which said elliptically polarizing means is a retardation plate through which said probe laser output passes.

27. The improvement according to claim 21 in which said polarization analyzer is a Glan-Thompson type prism and said prism is disposed so that portions of said probe laser output and said shifted probe laser output are passed, said passed portions having the same polarization, said passed probe laser output comprising a local oscillator output, said optical heterodyning means comprising said detection means at which said probe laser output and said shifted probe laser output are combined thereby forming said heterodyned cross-term signal.

28. The improvement according to claim 18 in which said pump laser output is circularly polarized.

29. The improvement according to claim 18 in which said pump laser output is linearly polarized.

30. The improvement according to claim 18 further comprising:
means for processing said heterodyned cross-term signal; and
means for monitoring said processed heterodyned cross-term signal.

31. The improvement according to claim 30 further comprising:
means for modulating said pump laser output thereby resulting in a modulated heterodyned cross-term signal; and
said processing means further comprising means to selectively amplify said modulated heterodyned cross-term signal.

32. In an apparatus for detecting coherent Raman signals from a Raman-active sample comprising a pump laser having a circularly polarized output radiation at a frequency $w_1$, a probe laser having a linearly polarized output radiation at a frequency $w_2$, $w_1-w_2$ approximating a Raman mode frequency of said sample thereby resulting in a first portion of said probe laser output shifting polarization by 90 degrees as it passes through said sample, means for directing said probe laser output and said pump laser output into said sample whereby to intersect each other within said sample, a polarization analyzer for passing some of said probe laser radiation having a predetermined polarization after having passed through said sample, and means for detecting radiation that has passed through said analyzer, the improvement comprising means for passing through said polarization analyzer portions of said probe laser output not having shifted polarization and portions of said probe laser output having shifted polarization by 90 degrees, said not-shifted portion of said probe laser output constituting a local oscillator output; said probe laser outputs having passed through said polarization analyzer and combined at said detection means thereby forming a heterodyned corss-term signal linearly proportional to the Raman cross section of said sample.

33. In an apparatus for detecting coherent Raman signals from a Raman active sample comprising a pump laser having a circularly polarized output radiation at a frequency $w_1$, a probe laser having a linearly polarized output radiation at a frequency $w_2$, $w_1-w_2$ approximating a Raman mode frequency of said sample thereby resulting in a first portion of said probe laser output shifting polarization by 90 degrees as it passes through said sample, means for directing said probe laser output and said pump laser output into said sample whereby to intersect each other within said sample, a polarization analyzer for passing radiation having the same polarization as that portion of said probe laser output having its polarization shifted by 90 degrees, and means for detecting radiation that has passed through said polarization analyzer, the improvement comprising means for isolating a portion of said probe laser output to be used as a local oscillator signal and combined with said polarization-shifted portion of said probe laser output, said combined portions thereby forming a heterodyned cross-term signal linearly proportional to the Raman cross-section of said sample.

34. The improvement according to claim 33 in which said isolating means comprises a first beam splitter through which said probe laser output passes before entering said sample, a reflected portion of said probe laser output from said first beam splitter being routed by reflecting plates and a second beam splitter to said detection means, said reflected portion constituting said local oscillator signal.

35. The improvement according to claim 33 further including means for elliptically polarizing said probe laser output thereby creating a second portion of said probe laser output having the same polarization as the polarization-shifted portion of said probe laser output, said second portion comprising said local oscillator signal, said first and second probe laser output portions passing through said polarization analyzer and combining at said detecting means thereby creating said heterodyned cross-term signal.

36. In an apparatus for detecting coherent Raman signals from a Raman active sample comprising a pump laser having a circularly polarized output radiation at a frequency $w_1$, a probe laser having a linearly polarized output radiation at a frequency $w_2$, $w_1-w_2$ approximately a Raman mode frequency of said sample thereby resulting in a first portion of said probe laser output shifting polarization by 90 degrees as it passes through said sample, means for directing said probe laser output and said pump laser output into said sample whereby to intersect each other within said sample, a polarization analyzer for only passing radiation having a polarization the same as said probe laser first portion, and means for detecting radiation that has passed through said polarization analyzer, the improvement comprising means for changing a second portion of said probe laser output so that subsequent to passage though said sample it has the same polarization as said probe laser first portion, said second portion comprising a local oscillator signal, said first and second probe laser portions when combined at said detecting means creating a heterodyned cross-term signal linearly proportional to the Raman cross-section of said sample.

37. The improvement according to claim 36 in which said changing means comprises means for elliptically polarizing said probe laser output prior to its entrance into said sample, said elliptically polarized probe laser output comprising said probe laser second portion.

38. In an apparatus for detecting coherent Raman signals from a Raman-active sample comprising a pump laser having a circularly polarized output radiation at a frequency $w_1$, a probe laser output having a linearly polarized output radiation at a frequency $w_2$, $w_1-w_2$ approximating a Raman mode frequency of said sample thereby resultng in a first portion of said probe laser output shifting polarization by 90 degrees as it passes through said sample, means for directing said probe laser output and said pump laser output into said sample whereby to intersect each other within said sample, a polarization analyzer for only passing radiation having a polarization the same as said probe laser first portion, and means for detecting radiation that has passed through said polarization analyzer, the improvement comprising means for routing a second portion of said probe laser output prior to its entrance into said sample to said detecting means and bypassing said sample and said polarization analyzer, said second portion comprising a local oscillator signal, said first and second probe laser portions when combined at said detecting means creating a heterodyned cross-term signal linearly proportional to the Raman cross-section of the sample.

39. The improvement according to claim 38 further comprising means for adjusting the phase of said probe laser second portion with respect to the phase of said probe laser output.

* * * * *

UNITED STATES PATENT AND TRADEMARK OFFICE
CERTIFICATE OF CORRECTION

PATENT NO. : 4,193,690
DATED : March 18, 1980
INVENTOR(S) : Marc D. Levenson et al It is certified that error appears in the above-identified patent and that said Letters Patent are hereby corrected as shown below:

Col. 4, line 59, after "laser" add --16--.

Col. 8, line 40, delete "route" and substitute therefor --routed--.

Col. 9, line 65, delete "corss-term" and substitute therefor --cross-term--.

Col. 10, line 43, delete "approximately" and substitute therefor --approximating--.

Signed and Sealed this

Twenty-second Day of July 1980

[SEAL]

Attest:

SIDNEY A. DIAMOND

Attesting Officer     Commissioner of Patents and Trademarks